United States Patent [19]

Philip

[11] Patent Number: 4,898,576
[45] Date of Patent: Feb. 6, 1990

[54] INTRAVENOUS FLUID FLOW MONITOR

[76] Inventor: James H. Philip, 75 Francis St., Boston, Mass. 02115

[21] Appl. No.: 236,341

[22] Filed: Aug. 22, 1988

Related U.S. Application Data

[63] Continuation of Ser. No. 81,613, Jul. 31, 1987, abandoned, which is a continuation of Ser. No. 872,199, Jun. 6, 1986, abandoned.

[51] Int. Cl.$^4$ ............................................. A61M 5/14
[52] U.S. Cl. ......................................... 604/50; 604/65
[58] Field of Search ................................... 604/50–53, 604/65–67, 93, 118, 245–246, 31, 149; 128/DIG. 13; 73/861, 861.42, 861.47, 861.52

[56] References Cited

U.S. PATENT DOCUMENTS

| | | | |
|---|---|---|---|
| 4,526,574 | 7/1985 | Pekkarinen | 128/DIG. 13 X |
| 4,530,696 | 7/1985 | Bisera et al. | 604/67 X |
| 4,534,756 | 8/1985 | Nelson | 604/50 |
| 4,619,653 | 10/1986 | Fischell | 128/DIG. 13 X |

Primary Examiner—Angela D. Sykes
Attorney, Agent, or Firm—Fulwider, Patton, Lee & Utecht

[57] ABSTRACT

An improved system for monitoring the fluid flow through a fluid delivery system to a patient wherein the fluid flow rate is varied in a predetermined sequential manner. Corresponding changes in pressure in the line connecting the vein of a patient and the pump are detected and are used to derive signals indicative of the resistance or impedance in the line, which in turn can be used to determine whether the vein is normal, whether it is phlebitic, whether it is occluded, whether infiltration of the canula into the patient's soft tissue has occurred, or whether the continuity of tubing to the vein has been interrupted.

23 Claims, 3 Drawing Sheets

INTRAVENOUS FLUID FLOW MONITOR

This application is a continuation of application Ser. No. 081,613, filed July 31, 1987, now abandoned which is a continuation of Ser. No. 872,199 filed June 6, 1986, now abandoned.

FIELD OF THE INVENTION

This invention relates to an apparatus for monitoring the flow of intravenous fluid through a parenteral fluid delivery system into a patient's vein. More particularly, the invention relates to apparatus and methods for detecting on a real time basis whether such a fluid is flowing successfully into the patient's vein, whether it is infiltrating the soft tissue surrounding the vein, whether the vein is occluded, whether the vein is phlebitic or whether the cannula has been detached completely from the patient's vein, or if any other disconnection has occurred.

BACKGROUND OF THE INVENTION

The addition of parenteral fluids to the blood streams of patients by means of cannulas inserted into the veins has been conventional for many years. More recently, parenteral systems have been introduced in which the fluids are positively pumped into the patient's veins, as opposed to earlier systems in which gravity was the motivating force. Pumping has become prevalent because it permits more precise control of fluid flow. Still more recently, systems have been developed in which the pressure in the line connecting the pump to the vein is monitored and a pressure signal is transmitted to a microprocessor or similar device for continuous monitoring of the pressure, so as to determine whether the pressure is within certain limits indicative of proper fluid flow. The goal of such instruments is to provide an indication of whether the cannula is properly in the vein, whether the vein flow is normal, and so on. See, for example, U.S. Pat. No. 4,460,355 to Layman, in which a further problem is addressed, that of distinguishing spikes in the fluid pressure due to the discontinuous action of the pump from pressure changes due to abnormal conditions which should be detected so as to give an alarm. The Layman patent provides means for only measuring the pressure of the pumping cycle during certain periods when pressure spikes caused by the pump action may be presumed not to be present.

The applicant is also aware of U.S. Pat. No. 4,534,756, assigned to the present assignee, entitled "Fault Detection Apparatus And Method For Parenteral Infusion System." This application broadly discloses a system in which the pressure waveform generated by a pump which produces a pulsating pressure waveform is monitored from cycle to cycle. When a change in the waveform out of preset limits is detected, an alarm is given. While this system was a substantial advance, it frequently could not distinguish fluid flow faults from normal pressure variations particularly at high flow rates.

Accordingly, the art requires an improved intravenous flow monitor which is capable of distinguishing between actual problems, e.g. occlusion of the vein, a cannula becoming detached from the patient's arm, or penetrating through or being withdrawn from the vein so as to be disposed in the surrounding soft tissue, and between artifacts such as relative changes in elevation of the pump and the point of injection of the fluid into the patient.

SUMMARY AND OBJECTS OF THE INVENTION

It is an object of the invention to provide an intravenous flow monitor which can successfully distinguish between real fluid flow problems and artifacts caused by relative vertical motion of the patient's injection point and the pump.

The present inventor has realized that what is needed is an actual measurement of the resistance to flow characteristic of the tissue into which the fluid is being injected. To provide such an indication of resistance to flow provides accurate flow monitoring, regardless of the absolute pressure in the line.

Accordingly, it is an object of the invention to provide an intravenous flow monitor which provides an actual indication of the resistance to flow at the point of insertion of the cannula.

The present inventor has realized further that, given an actual measurement of the resistance to flow, one can then further determine the location of the cannula. For example, the resistance to flow of a phlebitic or occluded vein can be differentiated from the resistance to flow of a normal vein. Similarly, should the cannula penetrate through the vein (a condition referred to as "infiltration"), such that the parenteral fluid is being pumped into the tissue surrounding the vein, this can also be detected. As will be recognized by those skilled in the art, infiltration is a serious condition which can lead to injury. Similarly, a measure of the resistance to flow can readily provide an indication that the catheter has become disconnected.

Accordingly, it is an object of the invention to provide an improved intravenous flow monitor which provides a measure of the resistance to flow of fluid in the line connecting the source of fluid and the cannula, and which furthermore used such measurement to provide an indication of the conditions at the end of the cannula, i.e. occluded vein, healthy vein, phlebitic vein, disconnection, infiltration, and so forth.

The present invention meets the needs of the art and objects of the invention discussed above by its provision of an improved intravenous pressure monitor in which a peristalitic or other pump is controlled by a microprocessor on an equivalent device to increase and decrease the flow rate, and in which the change in pressure in the fluid line connecting the pump and the patient responsive thereto is monitored.

The present inventor has discovered that when the parenteral fluid flow rate is varied by a relatively small amount, the ratio of the change in pressure to the change in fluid flow rate is the "dynamic resistance" in the line, this term being used to refer to the resistance sensed with respect to a perturbation in flow rate which is small compared to the flow rate and a responsive perturbation in pressure. If resistance is taken to be equal to the thus-computed dynamic resistance, by comparing the resistance in the line to values predetermined by experiment, one can determine the conditions at the cannula. Thus, for example, if the cannula has become detached completely from the patient, there will be substantially no resistance and the pressure will change very little with change in flow rate. On the other hand, if the cannula has entered an occluded vein, typically the pressure will change significantly with changes in flow rate.

In the preferred embodiment, the microprocessor also monitors the rise time of changes in the pressure; for example, if a square wave change is provided in the flow rate, the corresponding change in the pressure will be somewhat rounded. By monitoring the extent of this rounding, one can differentiate between certain other conditions. For example, the resistance to flow of phlebitic vein in some cases can be substantially equal to the resistance to flow of the soft tissue typically surrounding veins, such that a phlebitic vein could not be distinguished from infiltration merely by monitoring the resistance to flow. However, the inventor has found that the rise time of the pressure changes resulting from square-edged changes in the rate can be used to differentiate between these two conditions.

BRIEF DESCRIPTION OF THE DRAWINGS

The invention will be better understood if reference is made to the accompanying drawings in which.

DESCRIPTION OF PREFERRED EMBODIMENTS

Figure 1:
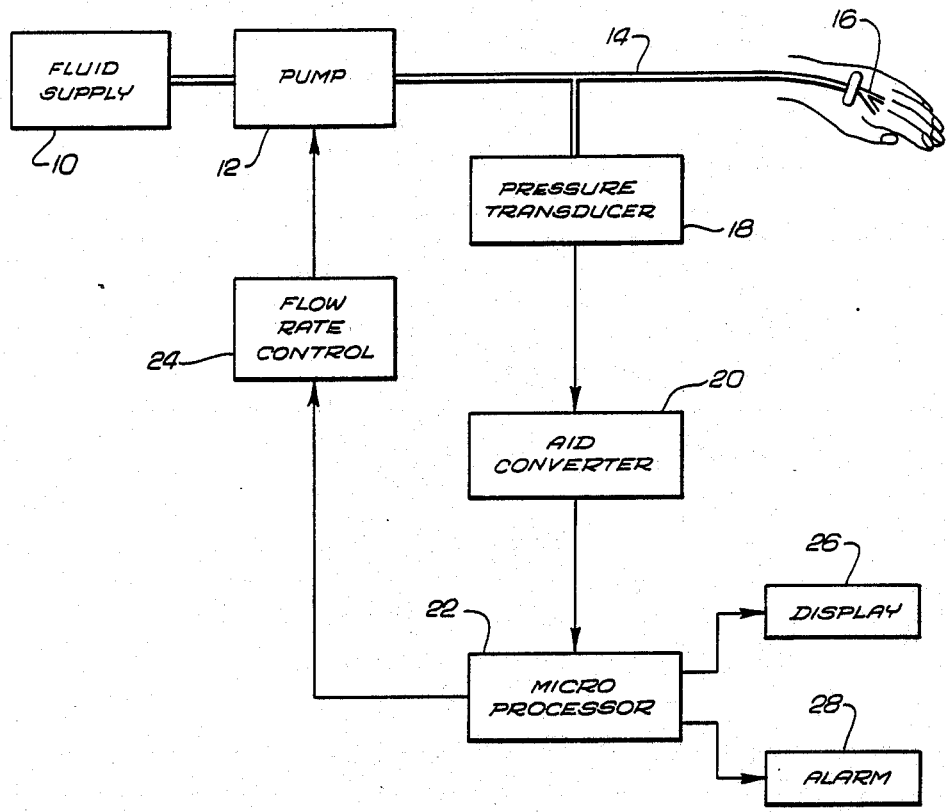
FIG. 1 shows a schematic view of the apparatus used to provide intravenous flow monitoring according to the invention.

As shown in FIG. 1, the system embodying features of the invention generally comprises a fluid supply 10 of any desired parenteral fluid and a pump 12, which may typically be a peristaltic pump to which is connected a tube 14 which in turn is connected to a cannula 16 inserted into the vein of a patient. The pressure in the line 14 is monitored by a pressure transducer 18 which is connected to an analog-to-digital converter 20 for supplying digital data representing the pressure in the tube 14 to a microprocessor 22. The microprocessor 22 provides output signals to a flow rate controller 24 which controls the rate of flow delivered by the pump 12. The microprocessor 22 also provides an operator display 26 and can generate an alarm signal at 28 when certain conditions discussed in detail below are detected. The microprocessor 22 is also enabled to accept operator input for controlling the rate of flow and the like.

According to the present invention, the fluid flow rate is sequentially varied and the difference in pressure caused by the variations in flow rate is noted. By comparing these two values, the instrument can determine the dynamic resistance to flow in the line, which is in turn a measure of the resistance to flow in the environment at the end of the catheter, e.g. in a patient's vein, the tissue surrounding the vein, or the like.

Figure 2:
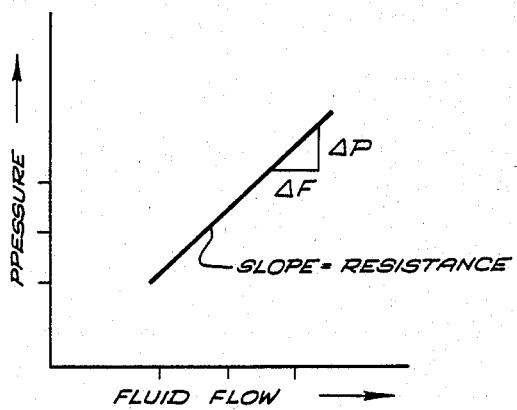
FIG. 2 shows a typical plot of flow rate versus pressure.

FIG. 2 shows a graph of pressure P versus flow rate F and indicates how measurement of the dynamic resistance can be derived. The operator will have set the initial flow rate at some value $F_s$. A corresponding value for the pressure $P_s$ is detected by the pressure transducer 18. The microprocessor then sequentially varies the flow rate F about $F_s$ in one or both directions. The pressure transducer detects corresponding variations in the pressure P as indicated on FIG. 2. Two or more points indicating corresponding values for the flow rate and pressure can then be connected, and the slope of the resulting line is equivalent to the dynamic resistance to flow at the end of the cannula.

As described above, this "dynamic resistance," as it is termed herein, is not a measurement of the absolute resistance to flow, because no absolute pressure measurement is made. The measurement in effect is of the resistance to fluid flow variation. The term "resistance" is used in the claims of this application, and should be so understood. The inventor herein has found that a clinically useful measurement is provided.

Figure 3A:
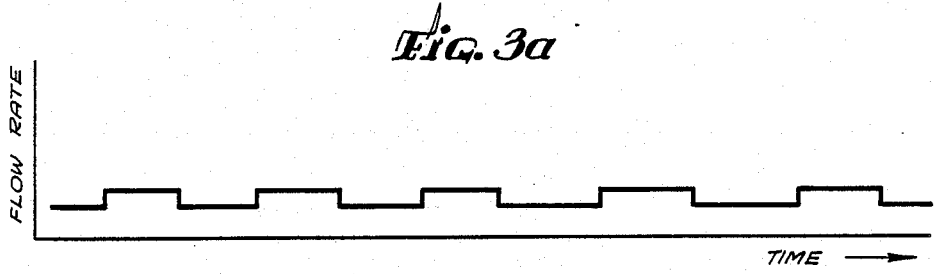
FIGS. 3a and 3b shown typical signal waveforms, FIG. 3a showing changes in the flow rate, and FIG. 3b showing corresponding pressure changes.
Figure 3B:
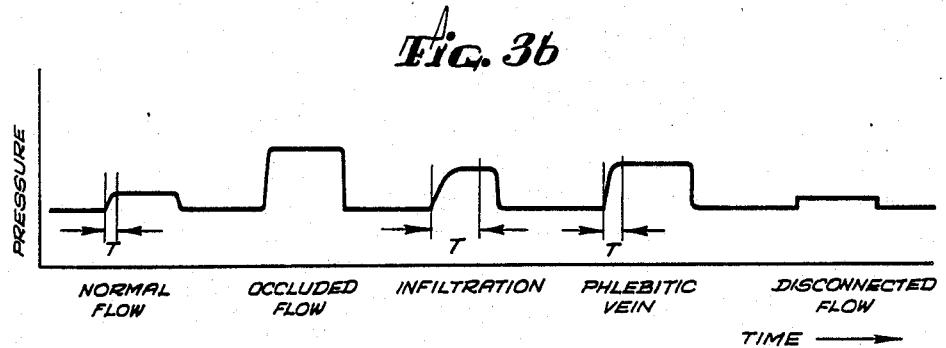

FIG. 3 comprises FIGS. 3A and 3B, which show typical input fluid flow rate changes and typical detected changes in pressure, respectively. The first condition, represented by the initial change, is for a normal vein; in response to the square edged change in the flow rate, the pressure changes correspondingly. As noted, the change appearing in the pressure waveform is somewhat rounded, having a "rise time" T. This is due to compliance in the lines connecting the pump and the vein, as well as compliance of the normal vein itself.

The second case shown is that of an occlusion in the vein or the connecting tubing. There the change in the flow rate is responded to by a very high change in the pressure, due to the blockage of the occluded vein or tubing.

The third case shown is of an infiltrated vein, that is, one which the cannula has actually penetrated through the vein and is in the soft tissue surrounding the vein. There, the pressure rises substantially, but over a period of time T as the parenteral fluid is pumped into the soft tissue. As is well known, this can be a serious condition leading at least to local or more generalized tissue damage.

The fourth condition shown is that of a phlebitic vein, in which the vein tends to be stiffer than usual, as well as possibly having some constriction therein. Here, the pressure rise is comparable to that shown in the infiltrated case, but occurs much more quickly, due to the stiffness of the vein. Measurement therefore of the rise time T can provide a way of differentiating between these two conditions, as discussed below in connection with FIG. 4.

Finally, the last condition, disconnection, is shown. There, the change in flow rate causes a very minimal change in pressure due to the open-ended cannula or tubing having become disconnected from the patient.

It will be appreciated by those skilled in the art that, if the flow rate change is always the same, as shown in FIG. 3A, there is no real need to compare the change in flow rate to the change of pressure, as the pressure change and the rise time T are all that would be needed to distinguish between the various conditions shown. However, as will be discussed below, frequently the flow rate change must vary. Hence it is the better practice to in fact calculate the dynamic resistance R by dividing the amplitude of the pulse in the pressure waveform of FIG. 3B by the height of the flow rate pulse of FIG. 3A.

Figure 4:
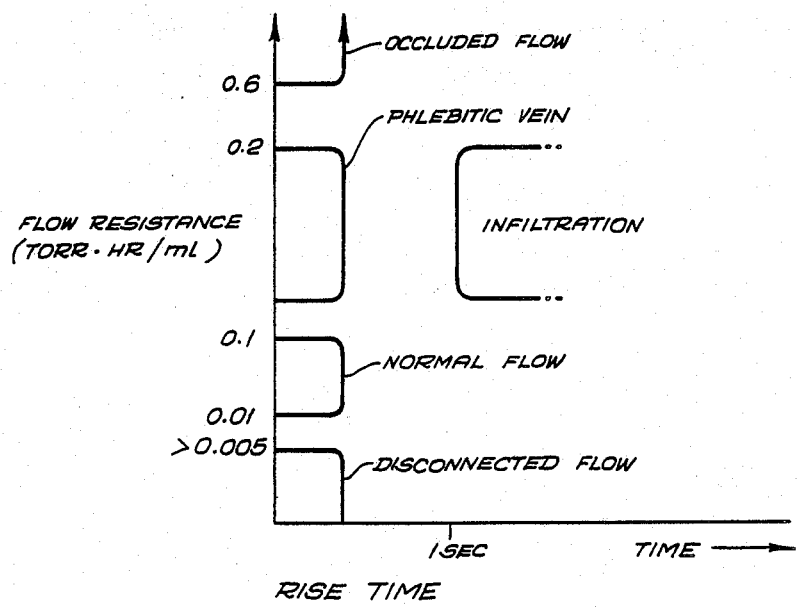
FIG. 4 shows a graph of the absolute value of the resistance in the line compared to the rise time for various conditions.

FIG. 4 shows a plot of actual data, showing the relationship of the absolute value of the dynamic resistance of the vein R, in torr * hr/ml versus the rise time of the pulse T; a number of areas are delineated on the chart to indicate experimental variation and the like. As shown, a disconnected cannula produces very low resistance; a normal vein shown a somewhat higher range of resistance; a phlebitic vein is higher still; and an occluded vein is highest of all. As shown, an infiltration condition gives a value for resistance to flow which is more or less equivalent to that of a phlebitic vein, but has a much higher rise time T.

Accordingly, all that is required to detect the various conditions is to compare the relative resistances to flow and where there is ambiguity, to further examine the rise time of the pressure change.

Figure 5:
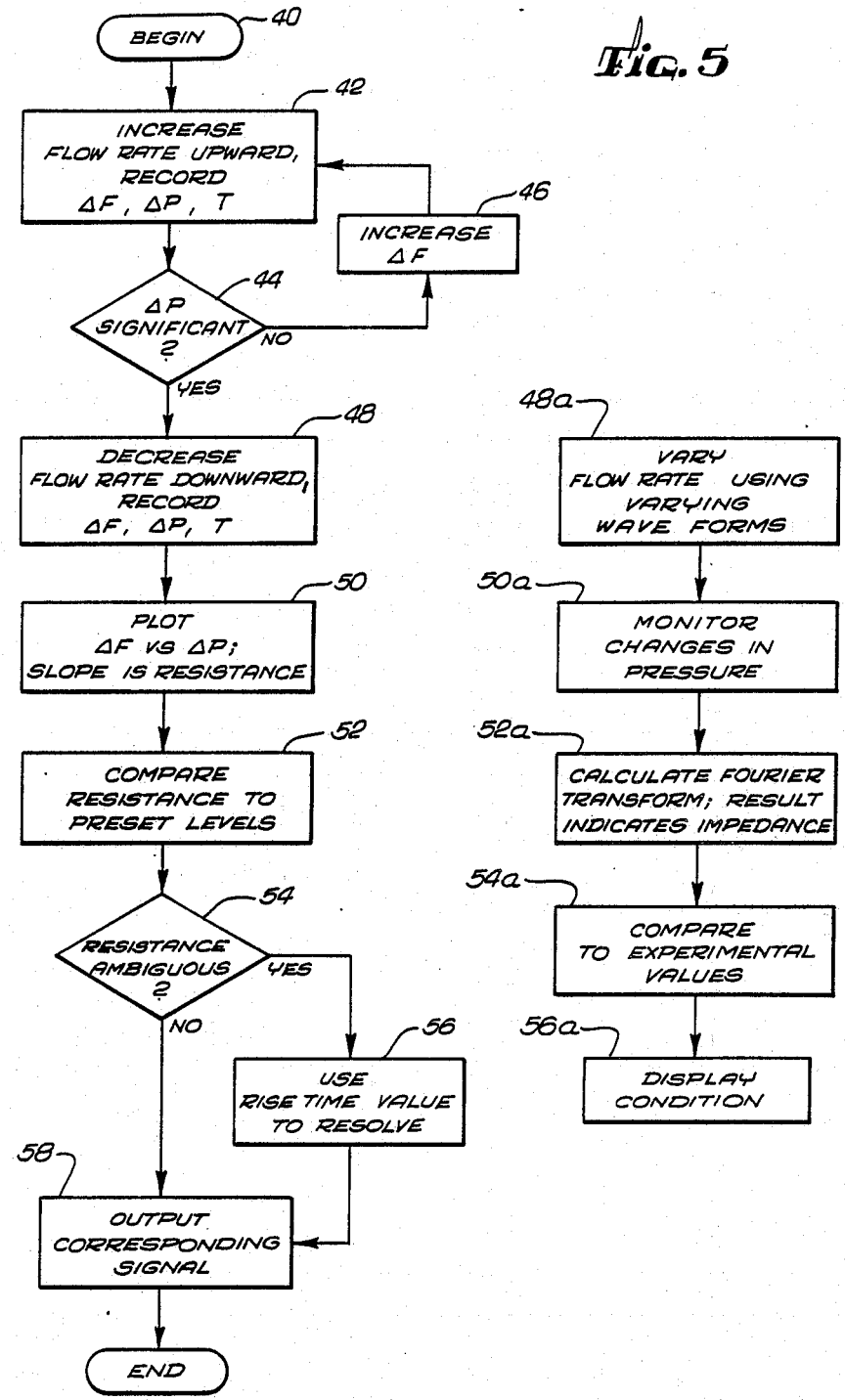
FIG. 5 shows a flow chart of the more significant steps in the processing performed by the microprocessor.

FIG. 5 shows the flow chart according to which the microprocessor performs these operations. Processing begins at step 40. The first step 42 is to increase the flow rate and to record a change in flow rate $\Delta F$, a change in pressure $\Delta P$ and the rise time T. At step 44, $\Delta P$ is compared to certain preset limits. This is because flow rates can vary quite widely, between on the order of millitiers per hour to liters per hour. Accordingly, to simply vary the flow rate by some fixed amount might not always yield a statistically significant change $\Delta P$ in the line pressure. Similarly, it may cause non-physiologic extreme changes in pressure. Accordingly, $\Delta P$ is compared to preset limits. If $\Delta P$ is statistically insignificant, the flow rate change $\Delta F$ is altered at step 46 and the process in reperformed. This may be done by the microprocessor automatically, by the operator, or by an interactive combination of both. When suitable values of $\Delta P$ are determined, the same procedure is performed by decreasing the flow at step 48 and again recording $\Delta F$, $\Delta P$ and T. At step 50, the slope of the line connecting the corresponding values for P and F is calculate. The slope of this line is the resistance R. At step 52, the resistance is compared to preset levels established by experimentation. If the resistance value is ambiguous, as tested at step 54, then the rise time value T is evaluated at step 56. After resolution, if needed, the corresponding output signal is generated at step 58, e.g., on the display 26 (FIG. 1).

The rise time T can be simply calculated by programming the microprocessor 22 to take the time derivative of the pressure signal, which would typically be sampled at regular intervals, e.g. every 10 msec. When the derivative is within some predetermined distance from zero, indicating that he pressure pulse has substantially reached its peak, this can be taken as the cut-off point, so that the time between the sending of the flow rate pulse signal to the flow rate controller 24 (FIG. 1) and this point is the rise time T. Other well known rise time measurement techniques (e.g., mean transit time measurement techniques) are with the skill of the art.

A further improvement can be made by increasing the sophistication of the signal processing system, e.g., by performing a Fourier analysis in order to determine the information directly relevant to the system's impedance to flow over a spectrum of frequencies. To implement such an approach would typically require use of more complex variation in the flow rate. Sinusiodal and white noise variation may be used, as indicated by step 48a of FIG. 5, which substitutes for step 48 according to this alternative embodiment. Steps 50a-56a shown the remaining processing steps in this alternative embodiment. In step 50a the pressure in the line is monitored as a function of the change in flow rate. At step 52a, the Fourier transform is taken of this data; the result is the actual impedance to flow of the tissues at the end of the catheter. At step 54a the impedance thus determined is compared to experimentally determined values, and at step 56a the corresponding condition is displayed.

Given the above disclosure, those skilled in the art would have no difficulty implementing the present invention. Note that the main hardware elements of this system, the peristaltic pump 12 controlled by the microprocessor 22 and the pressure transducer 18, are commercially available. However, the microprocessor should be programmed to provide panel displays and/or alarms responsive to the various conditions detected by the system of the invention, and establishing the levels for comparison to the signals. Typical values for R and T are indicated on FIG. 4.

While a preferred embodiment of the invention has been described, those skilled in the art will recognize that there are additional modifications and improvements which can be made thereto without departure from its spirit and scope. The invention is therefore not to be limited by the above exemplary disclosure, but only by the following claims.

What is claimed is:

1. A system for monitoring the flow of fluid through a fluid delivery system to a patient comprising:
   (a) means for monitoring fluid pressure in the fluid delivery system supplying fluid to a patient;
   (b) means for controlling the fluid flow through the fluid delivery system at sequentially different flow rates in a predetermined manner;
   (c) means responsive to the sensed pressures and the sequentially different fluid flow rates, for determining resistance to fluid flow in the fluid delivery system; and
   (d) means for comparing the determined resistance with predetermined limits and for generating output signals responsive thereto.

2. The system of claim 1, wherein the means for determining the resistance to fluid flow in the fluid delivery system and the means for comparing the determined resistance to predetermined limits is a microprocessor.

3. The system of claim 2, wherein the microprocessor further comprises means for monitoring the time rate of change of pressure in the fluid delivery system which is responsive to sequential differences in the flow rate of the fluid.

4. They system of claim 3 wherein the microprocessor includes means to calculate from the time rate change of pressure in the fluid delivery system the mean transit time of sequential differences in the flow rate of the fluid.

5. The system of the claim 3 wherein the microprocessor includes means to calculate from the time rate of change of pressure in the fluid delivery system a time constant which is responsive to sequential differences in the fluid flow rate in the fluid delivery system.

6. The system of claim 2, wherein the means for monitoring the pressure in the fluid delivery system is a pressure transducer outputting an analog signal, and the system further comprises analog-to-digital converter means for conversion of the analog signal to a digital signal for supply to the microprocessor.

7. The system of claim 2, wherein the microprocessor includes means to calculate resistance from the changes in pressure with respect to the sequential differences in flow rate, to provide a resistance value.

8. The monitor of claim 7, wherein the microprocessor further comprises means for determining the rate of change of pressure with respect to time.

9. The system of claim 1, wherein the fluid flow control means includes means to generate variations in fluid flow rates having a predetermined frequency spectrum.

10. The system of claim 9, wherein the microprocessor comprises means for taking the Fourier transform of variations in the pressure which are responsive to the variations in the flow rate.

11. The system of claim 9, wherein said microprocessor further comprises means for calculating the time derivative of changes in the pressure.

12. The system of claim 1, wherein the means for supplying fluid at controllable flow rates comprises means for causing the flow rates to be varied in a manner having a defined frequency component, and wherein the means for determining resistance to flow comprises means for analyzing the variations in pressure which are responsive to the variations in flow rates.

13. A method for monitoring the flow of fluid through a fluid delivery system to a patient comprising:
   (a) monitoring fluid pressure in the fluid delivery system supplying fluid to a patient;
   (b) controlling the fluid flow through the fluid delivery system at sequentially different flow rates in a predetermined manner;
   (c) determining resistance to fluid flow in the fluid delivery system in response to the sensed pressure and to the sequentially different fluid flow rates; and
   (d) comparing the determined resistance to predetermined limits and generating output signals responsive thereto.

14. The method of claim 13 including calculating the rate of change of pressure in the fluid delivery system with respect to time which is responsive to the sequential differences in flow rate of the fluid.

15. The method of claim 14 wherein the changes in pressure with respect to the sequential variations in flow rate are determined in order to determine a resistance to fluid flow.

16. The method of claim 15, wherein the time rate of change of pressure is calculated.

17. The method of claim 13 including calculating the mean transit time of the sequential differences in the flow rate of the fluid.

18. The method of claim 13 including calculating a time constant for changes in the pressure which is responsive to the sequential differences in the flow rate in the fluid delivery system.

19. The method of claim 14 including generating an analog signal representing the monitored pressure and converting the analog signal to a digital signal.

20. The method of claim 13, wherein the sequential variations in flow rates have a predetermined frequency spectrum.

21. The method of claim 20, including determining the Fourier transforms of variations in the pressure which are responsive to sequential variations in the flow rate.

22. The method of claim 21, wherein the time derivative of changes in the pressure is calculated.

23. The method of claim 20, wherein the fluid is supplied at controllable flow rates which are sequentially varied in a manner having a defined frequency content, and resistance to flow is determined by analyzing the sequential variations in pressure which are responsive to the sequential variations in flow rates.

* * * * *

UNITED STATES PATENT AND TRADEMARK OFFICE
CERTIFICATE OF CORRECTION

PATENT NO. : 4,898,576

DATED : February 6, 1990

INVENTOR(S) : James H. Philip

It is certified that error appears in the above-identified patent and that said Letters Patent is hereby corrected as shown below:

Column 2, line 39, delete "used" and insert therefor --uses--.
Column 2, line 46, delete "peristalitic" and insert therefor --peristaltic--.
Column 2, line 47, delete "on" and insert therefor --or--.

Column 3, line 25, delete "shown" and insert therefor --show--.

Column 5, line 1, delete "shown" and insert therefor --shows--.
Column 5, line 17, delete "millitiers" and insert therefor --milliliters--.
Column 5, line 27, delete "of" and insert therefor --for--.
Column 5, line 31, delete "calculate" and insert therefor --calculated--.
Column 5, line 44, delete "he" and insert therefor --the--.
Column 5, line 50, delete "with" and insert therefor --within--.
Column 5, line 57, delete "sinusiodal" and insert therefor --sinusoidal--.
Column 5, line 60, delete "shown" and insert therefor --show--.

In the Claims:

Claim 4, Column 6, line 43, delete "They" and insert therefor --the--.

UNITED STATES PATENT AND TRADEMARK OFFICE
CERTIFICATE OF CORRECTION

PATENT NO. : 4,898,576
DATED : February 6, 1990
INVENTOR(S) : James H. Philip

It is certified that error appears in the above-indentified patent and that said Letters Patent is hereby corrected as shown below:

Claim 5, Column 6, line 48, delete the first appearance of "the".

Signed and Sealed this

Thirteenth Day of December, 1994

Attest:

BRUCE LEHMAN

*Attesting Officer*  *Commissioner of Patents and Trademarks*